(12) United States Patent
Murthy

(10) Patent No.: US 11,602,288 B2
(45) Date of Patent: *Mar. 14, 2023

(54) MONITOR AND SYSTEM FOR MONITORING AN ORGANISM

(71) Applicant: ATONARP INC., Tokyo (JP)

(72) Inventor: Prakash Sreedhar Murthy, Tokyo (JP)

(73) Assignee: ATONARP INC., Tokyo (JP)

( * ) Notice: Subject to any disclaimer, the term of this patent is extended or adjusted under 35 U.S.C. 154(b) by 491 days.

This patent is subject to a terminal disclaimer.

(21) Appl. No.: 16/687,729

(22) Filed: Nov. 19, 2019

(65) Prior Publication Data

US 2020/0155041 A1 May 21, 2020

Related U.S. Application Data

(63) Continuation of application No. 14/888,093, filed as application No. PCT/JP2014/002416 on May 2, 2014, now Pat. No. 10,517,516.

(30) Foreign Application Priority Data

May 2, 2013 (JP) ................................ 2013-096921

(51) Int. Cl.
A61B 5/1455 (2006.01)
A61B 5/00 (2006.01)
(Continued)

(52) U.S. Cl.
CPC .......... *A61B 5/1455* (2013.01); *A61B 5/0075* (2013.01); *A61B 5/14532* (2013.01);
(Continued)

(58) Field of Classification Search
CPC . A61B 5/1455; A61B 5/0075; A61B 5/14532; A61B 5/4839
See application file for complete search history.

(56) References Cited

U.S. PATENT DOCUMENTS 4,639,949 A 2/1987 Ales et al.
4,790,979 A 12/1988 Terminiello et al.
(Continued)

FOREIGN PATENT DOCUMENTS

CN 86 1 00100 A 8/1998
CN 101605494 12/2009
(Continued)

OTHER PUBLICATIONS

Office Action issued in corresponding Canadian Patent application No. 2,911,035, dated Feb. 1, 2021 (5 pages).
(Continued)

*Primary Examiner* — Marjan Fardanesh
(74) *Attorney, Agent, or Firm* — Buchanan Ingersoll & Rooney PC

(57) ABSTRACT

Provided is a monitor for monitoring the condition of the interior of a living organism from the surface of the living organism. The monitor is provided with: a probe which includes an observation window and is attached to the organism surface; a unit which irradiates, with a laser, at least a portion of an observation region; a unit which detects scattered light resulting from the laser irradiation; a Doppler analysis unit and a SORS analysis unit which narrow down the observation spots to a first observation spot; and a CARS analysis unit which obtains the optical spectrum for at least (Continued)

one component, and outputs first information indicating the condition of the organism interior on the basis of the intensity of the spectrum.

11 Claims, 7 Drawing Sheets

(51) Int. Cl.
*G01N 21/65* (2006.01)
*A61B 5/145* (2006.01)
(52) U.S. Cl.
CPC .......... *A61B 5/4839* (2013.01); *A61B 5/7275* (2013.01); *G01N 21/65* (2013.01); *A61B 2505/05* (2013.01); *A61B 2562/0238* (2013.01)

(56) References Cited

U.S. PATENT DOCUMENTS

| | | | |
|---|---|---|---|
| 5,045,282 | A | 9/1991 | Kritzman et al. |
| 6,558,351 | B1 | 5/2003 | Steil et al. |
| 2003/0212379 | A1 | 11/2003 | Bylund et al. |
| 2005/0147560 | A1 | 7/2005 | Yatscoff et al. |
| 2006/0240401 | A1 | 10/2006 | Clarke et al. |
| 2006/0276697 | A1 | 12/2006 | Demuth et al. |
| 2006/0281068 | A1 | 12/2006 | Maier et al. |
| 2007/0132994 | A1 | 6/2007 | Kobayashi et al. |
| 2007/0161876 | A1 | 7/2007 | Bambot et al. |
| 2007/0293766 | A1 | 12/2007 | Bakker et al. |
| 2008/0076985 | A1 | 3/2008 | Matousek et al. |
| 2008/0117416 | A1 | 5/2008 | Hunter |
| 2008/0188796 | A1 | 8/2008 | Steil et al. |
| 2010/0298685 | A1 | 11/2010 | Hayter et al. |
| 2012/0050720 | A1 | 3/2012 | Kim et al. |
| 2013/0261413 | A1 | 10/2013 | Kawahara et al. |

FOREIGN PATENT DOCUMENTS

| | | |
|---|---|---|
| CN | 102116929 A | 7/2011 |
| JP | 2003-522558 A | 7/2003 |
| JP | 2003-290345 A | 10/2003 |
| JP | 2007-020890 A | 2/2007 |
| JP | 2007-179002 A | 7/2007 |
| JP | 2007-192831 A | 8/2007 |
| JP | 2008-510559 A | 4/2008 |
| JP | 2008-522697 A1 | 7/2008 |
| JP | 2012-526982 A | 11/2012 |
| KR | 20100121807 A | 11/2010 |
| WO | WO 98/30889 A1 | 7/1998 |
| WO | WO 99/67623 A1 | 12/1999 |
| WO | WO 01/60246 A2 | 8/2001 |
| WO | WO 01/91626 A2 | 12/2001 |
| WO | WO 02/07585 A2 | 1/2002 |
| WO | WO 2004/016155 A2 | 2/2004 |
| WO | 2008052221 | 5/2008 |
| WO | WO 2012/049753 A1 | 4/2012 |

OTHER PUBLICATIONS

J Patrick Montoya "Membrane Gas Exchange Using Hollow Fiber Membranes to Separate Gases from Liquid and Gaseous Streams", MedArray, Inc.; 2010 (7 pages).

First Office Action issued in corresponding Chinese Patent Application No. 201811089639.6 dated Nov. 4, 2020, with English Translation (12 pages).

International Search Report (PCT/ISA/210) dated Jun. 24, 2014, by the Japanese Patent Office as the International Searching Authority for International Application No. PCT/JP2014/002416.

Montoya, Membrane Gas Exchange, MedArray, Inc., pp. 1-7, 2010.

Blakemore et al., Blood Vessels, The Oxford Companion of the Body, pp. 1-3, 2001.

Seylaz et al., Dynamic In Vivo Measurement of Erythrocyte Velocity and Flow in Capillaries and of Microvessel Diameter in Rat Brain by Confocal Laser Microscopy, Jour of Cerebral Blood Flow and Metabolism, 19, pp. 863-870, 1999.

Office Action and Search Report dated Oct. 19, 2018, by the Taiwanese Patent Office in corresponding Taiwanese Patent Application No. 10720953360. (10 pages).

Office Action (Notice of Examination Opinion) dated Jun. 8, 2018, by the Taiwanese Patent Office in corresponding Taiwanese Patent Application No. 10720506610. (7 pages).

Taiwanese Search Report dated Jun. 8, 2018, by the Taiwanese Patent Office in corresponding Taiwanese Application No. 10720506610. (1 pages).

R. Arora et al., "Analytical Capabilities of Coherent Anti-Stokes Raman Scattering Microspectroscopy", J Mod Opt., Nov. 1, 2008, pp. 3237-3254, vol. 55, No. 19-20.

C.L. Evans et al., "Coherent Anti-Stokes Raman Scattering Microscopy: Chemical Imaging for Biology and Medicine", Annual Review of Analytical Chemistry, Jul. 19, 2008, pp. 883-909, vol. 1.

X. Wang et al., "Glucose Concentration Measured by the Hybrid Coherent Anti-Stokes Raman-scattering Technique", Physical Review A, Jan. 20, 2010, vol. 81, 013813-1-013813-6.

Second Written Opinion dated Jan. 3, 2018, by the Intellectual Property Office of Singapore in corresponding Singaporean Application No. 11201508997R. (5 pages).

The Extended European Search Report dated Dec. 2, 2016, by the European Patent Office in corresponding European Patent Application No. 14791763.7-1657, (10 pages).

Search Report and Written Opinion dated Feb. 3, 2017, by the Intellectual Property Office of Singapore in corresponding Singaporean Patent Application No. 11201508997R. (10 pages).

Notification of Transmittal of Translation of the International Preliminary Report on Patentability (Forms PCT/IB/338 and PCT/IPEA/409) dated Nov. 5, 2015, by the International Bureau of WIPO in corresponding International Patent Application No. PCT/JP2014/002416. (10 pages).

Notification of Transmittal of Translation of the International Preliminary Report on Patentability (Forms PCT/IB/338 and PCT/IPEA/409) dated May 2, 2014, by the International Bureau of WIPO in corresponding International Patent Application No. PCT/JP2014/002416. (10 pages).

MONITOR AND SYSTEM FOR MONITORING AN ORGANISM

CROSS-REFERENCE TO RELATED APPLICATIONS

The present application is a continuation of U.S. Ser. No. 14/888,093, which is a national stage application of PCT/JP2014/002416, filed on May 2, 2014, and which claims the priority JP Application No. 2013-096921 which was filed on May 2, 2013. U.S. Ser. No. 14/888,093, PCT/JP2014/002416; and JP Application No. 2013-096921 are all incorporated herein by reference.

TECHNICAL FIELD

The present invention relates to a monitor for monitoring the internal state of an organism and a system that provides physiologically active substances based on information from a monitor.

BACKGROUND ART

Japanese Laid-Open Patent Publication No. 2007-192831 discloses a diagnostic kit capable of avoiding the need for invasive tests or the use of a blood marker in the measurement of glucose regulation. Such diagnostic kit is a diagnostic kit for measuring blood sugar regulation in a subject and includes a predetermined amount of enriched $^{13}C$ glucose and a respiration sampling container. The diagnostic kit includes a plurality of respiration sampling containers in one embodiment, is used for diagnosing diabetes in another embodiment, and is used for diagnosing insulin resistance in yet another embodiment.

DISCLOSURE

Although breath analysis is non-invasive, it is difficult to continuously monitor the state of an organism.

One aspect of the present invention is a monitor that monitors a state of an organism (living organism) internal part from a surface of the organism. The monitor includes: a probe including an observation window attached to the surface of the organism; a unit that emits a laser onto at least part of an observation region on the surface of the organism accessed via the observation window; a unit that detects scattered light caused by emission of the laser from each of a plurality of observation spots that are either intermittently dispersed in two dimensions in the observation region or are continuously formed so as to scan the observation region; a unit that limits, based on the scattered light obtained from the plurality of observation spots, from the plurality of observation spots to first observation spots where it is evaluated that scattered light including information on a target part of the organism internal part is obtained; and a unit that acquires spectra of at least one component from the first observation spots or peripheries of the first observation spots and outputs first information showing the state of the organism internal part based on intensities of the spectra.

It is desirable for the monitor to further include a unit that acquires spectra of a first component for a plurality of parts at different depths from the surface of the organism at the first observation spots or the peripheries of the first observation spots and further limits or updates the first observation spots based on the intensity of the spectra of the first component.

Another aspect of the present invention is a control method for a system including a monitor that monitors a state of an organism internal part from a surface of the organism. The monitor includes: a probe that sets a plurality of observation spots that are dispersed in two dimensions at first intervals on the surface of the organism; a unit that emits a laser onto the surface of the organism so that scattered light is outputted from each of the plurality of observation spots; and a unit that detects scattered light from the plurality of observation spots. The control method includes the following steps.

1. Acquiring scattered light from each of the observation spots in the plurality of observation spots and finding first observation spots relating to subcutaneous blood vessels out of the plurality of observation spots using a laser Doppler effect.
2. Acquiring spectra of a first component of a plurality of parts at different depths from the surface of the organism at the first observation spots or peripheries of the first observation spots and determining, based on intensities of the spectra of the first component, a target part below the surface of the organism.
3. Outputting first information showing the state of an internal part of the organism based on the intensities of the spectra of at least the first component at the target part.

It is desirable for the control method to further include the following step.

4. Acquiring spectra of the first component for a plurality of parts at different depths from the surface of the organism at the first observation spots or the peripheries of the first observation spots and further limiting or updating the first observation spots based on the intensity of the spectra of the first component.

It is possible to analyze compounds present in bodily fluids, such as blood, and subcutaneous tissues using spectroscopy technologies such as near-infrared spectroscopy and Raman spectroscopy, and to further analyze biochemical substances, cellular components, and the like in bodily fluids based on the analysis result. This means that it is definitely possible to acquire organism information by spectroscopy. However, the concentration of biochemical substances and cell composition differ at different parts of the organism. This means that the acquired information will include information of various structures below the surface of the organism, the target information may be buried in other information and noise, and it may be difficult to estimate the state of the organism.

With the monitor and control method described above, a plurality of observation spots are set in an observation region on the surface of an organism that can be accessed via the observation window of the probe. In addition, instead of using all data from the plurality of observation spots, spectra are acquired by locking onto some out of the plurality of observation spots using the unit that limits, and first information showing information on an internal part of the organism is outputted based on such data. Accordingly, since it is possible to selectively acquire information relating to a limited part below the surface of the organism, it is possible to avoid having the target information buried in other information or noise.

DETAILED DESCRIPTION OF PREFERRED EMBODIMENTS

Figure 1:
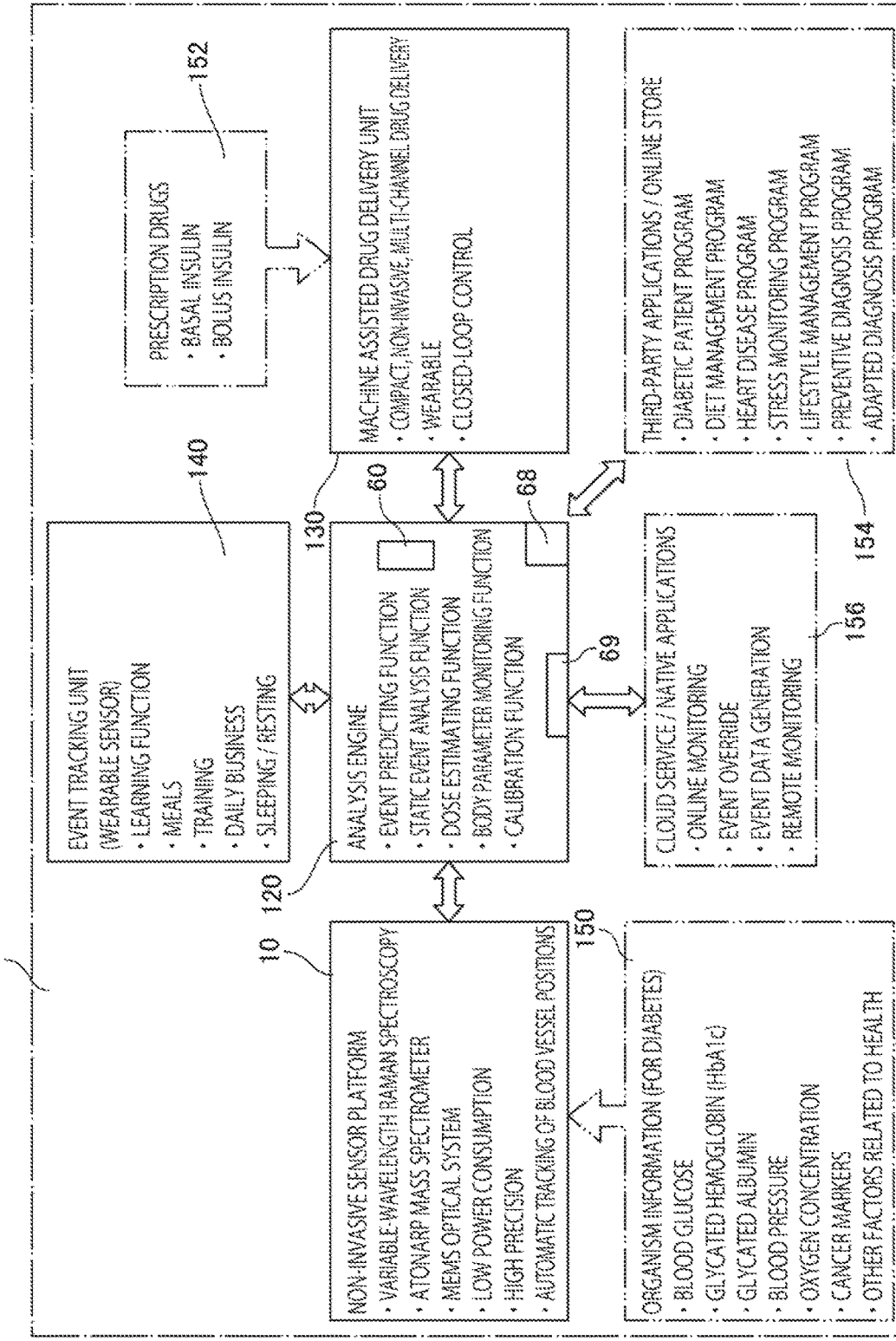
FIG. 1 is a block diagram showing a health management system.

An example case that has subcutaneous capillary vessels as a target and acquires information including an amount of a component (for example, glucose) flowing through the capillary vessels by acquiring spectra is described below.

The monitor according to the present invention sets a plurality of observation spots in an observation region on the surface of an organism (living organism, living body) that is accessible via an observation window of a probe. First, based on the scattered light obtained from the plurality of observation spots, a limiting unit first limits to, or locks onto, some of the observation spots where it is estimated that information on a target part of an organism internal part (a part of internal of a living organism) can be obtained as first observation spots. If the target part is a capillary vessel in the organism internal part, it is possible to focus on the spectra of laser Doppler effects included in the scattered light and to lock onto an observation spot as a first observation spot according to whether blood flow is observed at the observation spot. The target part is not limited to capillary vessels and in the case of lymph glands, it is possible to focus on the spectra of a component detected with the highest intensity when carrying out spectroscopic analysis of components included in lymph glands and to lock onto an observation spot as a first observation spot according to whether such component is observed at the observation spot.

Instead of merely finding a two-dimensional profile when locking onto the first observation spots, the limiting unit may find a three-dimensional profile that includes a profile in the depth direction. For capillary vessels, it is possible to calculate a profile in the depth direction from the blood flow component included in the laser Doppler effects using a mathematical model. When measuring Raman spectra, it is possible to use Spatially Offset Raman Spectroscopy (SORS).

It is assumed that the first observation spots where the blood flow of a capillary vessel are observed will be positioned corresponding above or near the capillary vessel. A unit that outputs first information that is organism information locks onto the first observation spots or observation spots in the periphery of or about the first observation spots, acquires spectra of at least one component, and outputs first information that shows the state and/or conditions of the organism internal part based on the intensity of the spectra.

With this monitor, it is effective to provide a unit that acquires spectra (spectrums) or a spectrum of a first component at a plurality of parts for different depths from the surface of the organism at the first observation spots or the peripheries thereof and further limits or updates the first observation spots based on the intensity of the spectra or the spectrum of the first component. It is possible to acquire spectra of a plurality of parts at different depths from the surface of the organism using spectrometry and to determine, from the intensity of the first component included in the spectra, the spectra or the spectrum of the target part. As one example, if it is desirable to detect the concentration of biochemical substances present in blood vessels, for a human subject, the vicinity of the organism surface is formed by the skin (epidermis) that forms the surface, the dermis, and subcutaneous tissues, with blood vessels (capillary vessels) often being present in the dermis or the subcutaneous tissues. However, the distance from the surface to the blood vessels differs according to the body part, also differs from patient to patient, and can also differ according to the patient's posture at such time.

With this monitor, by determining a spectrum where the intensities of the components present in the largest quantities in blood is the highest out of the spectra at different depths, it is possible to determine a spectrum of blood. By determining the intensities of one or a plurality of components included in a blood spectrum, it is possible to output first information showing the state of an internal part of an organism based on concentrations in blood. The target part is not limited to a blood vessel and may be subcutaneous fat or a lymph node or glands, and it is possible to generate first information showing the state of an organism internal part based on components of a plurality of target parts at different depths. Typical values for clinical biochemical analysis obtained from the spectrum of blood are cholesterol, blood sugar (glucose), glycated hemoglobin (such as HbA1c), AST, ALT, triglycerol, G-GTP, LDH, ALP, adiponectin, and the like.

One simple spectroscopic method for adjusting depth is a confocal Raman analysis. By using one or more confocal Raman analysis units, it is also possible to obtain three-dimensional information on components or cells present at a target part. Although the incident light for spectrometry may be LED light or light with a comparatively wide waveband, laser light of a narrow waveband is desirable. Using a tunable laser whose wavelength can be changed as a light source makes adjustment of depth easier and by carrying out resonance Raman spectroscopy, it is also possible to obtain a more precise spectrum of the target part.

Another example of a spectroscopic analysis method that can generate a profile in the depth direction is spatial offset Raman spectroscopy (SORS). In addition, as a method which can produce a profile in the depth direction with high precision, the present inventors has proposed the acquisition of a CARS spectrum that is spatially offset by controlling the incident angle (irradiation angle) of the pump light or Stokes light used in CARS (Coherent Anti-stokes Raman Spectroscopy (scattering).

The plurality of observation spots may be set by selectively emitting (irradiating) a laser onto a plurality of observation spots or scattered light may be selectively acquired from each of a plurality of observation spots. Accordingly, the probe may include an output unit that selectively guides the laser from the unit that emits to respective spots in the plurality of spots. The probe may include an input unit that guides the scattered light from the respective spots in the plurality of observation spots to the unit that detects. One example of the output unit and the input unit is a mirror or a group of mirrors (MD, Micromirror Device) that is formed by a MEMS or a micromachine. It is possible to form one or a plurality of laser spots intermittently or continuously inside the observation region and possible to form a large number of observation spots.

Another example of the output unit and the input unit is a combination of an optical member that forms multiple focal points, such as photonic crystal fiber (PCF), micro-structured fiber, Holey fiber or a bundle fiber, and a shutter matrix formed by a MEMS or a micromachine or an MD. It is possible to form one or a plurality of laser spots intermittently inside the observation region and possible to form a large number of observation spots.

It is desirable for the output unit and the input unit to be capable of setting a plurality of observation spots in the observation region at intervals of 1 to 1000 μm. It is even more preferable for the plurality of observation spots to be set at intervals of 10 to 100 μm in the observation region. The average size of subcutaneous tissues is several μm to several tens of μm, and it is preferable for the monitor to have a resolution of several hundred μm or smaller.

It is desirable for the probe to be tightly attached to the skin. Although it is possible to attach to the skin via a fluid such as gel, in view of user convenience and comfort, it is desirable for the observation window to be tightly attached to the surface of the skin via a diffusive porous membrane. Examples of diffusive porous membranes are membranes made of PDMS (polydimethylsiloxane) and hybrid silica.

By combining this monitor with a delivery unit that provides a physiologically active substance to the organism based on the first information obtained from the monitor, it is possible to provide a medication system. Such system is used to treat patients, to manage physical health, for rehabilitation, and the like. The physiologically active substance may be a biological material or a synthetic material, and represents a single substance or group of chemicals that has a physiological effect or a pharmacological effect on the organism. Physiologically active substances include vitamins, minerals, oxygen, and hormones, with one example of a hormone being insulin.

It is desirable for this system to include a behavior (movements) monitoring unit that acquires or predicts an external state (condition) of the organism. It is desirable for this system to further include a unit that controls an amount or type of physiologically active substance provided to the organism from the delivery unit according to information (second information) from the behavior monitoring unit in addition to the first information. By predicting the internal state (condition) of the patient in the near future from the patient's life rhythms and behavior patterns and/or predicting future changes in the organism from whether the patient is actually having a meal or exercising, it is possible to carry out prior control (advanced control) of the type and amount of physiologically active substances to be administered in accordance with the present state of the organism. This means that it is possible to control the type and amount of a physiologically active substance so that the state or conditions of the patient matches his/her behavior.

In addition, it is desirable for the system to include a unit that outputs the first information and an operating state of the delivery unit to outside (external). Via the system, it is possible for a doctor, nurse, or the like to remotely monitor a patient.

The control method for a system that includes the above monitor described in this specification can be provided as a program or a program product via the Internet or by being recorded on a suitable recording medium. This control method for a system may be provided as a method for monitoring the state of an organism internal part from the surface of the organism using spectrometry. This method may be provided as a method for treating a patient, may be provided as a method that manages the physical health or conditions of a user, or may be provided as a method for pre-emptively avoiding seizures or the like.

When the system includes a delivery unit that provides a physiologically active substance to the organism, it is desirable for the control method to further include a step of selecting a physiologically active substance and an amount to be delivered by the delivery unit based on the first information.

When the system further includes a behavior monitoring unit that acquires or predicts an external state of the organism, it is desirable for the step of selecting to include selecting the amount and/or type of physiologically active substance delivered by the delivery unit based on information on the external state in addition to the first information.

FIG. 1 shows, by way of a block diagram, the overall configuration of a non-invasive health and vitality control platform (control or adjustment system). This system 1 includes a sensor platform 10, an analysis engine 120, a drug delivery unit 130, and an event tracking unit 140. Note that although the system 1 that manages the health of a diabetic patient so as to keep the patient alive and to enable the patient to live a healthy and active life is described as an example in the following description, the disease to which the system 1 can be adapted as a platform is not limited to diabetes.

The sensor platform (monitor) 10 is capable of continuously and non-invasively monitoring the amount of glucose in the blood of a diabetic patient. One example of the sensor platform 10 is a variable wavelength FTIR-Raman spectroscopic analysis unit. The sensors mounted in the sensor platform 10 do not need to be of a single type and it is possible to use a plurality of types or to include a plurality of sensors of the same type. As examples, it is possible to collectively attach one or a plurality of types of sensors such as an infrared spectroscopic analysis apparatus, a near-infrared spectroscopic analysis apparatus, a mass spectrometry apparatus, and an ion mobility sensor to the surface of the organism, or to attach such sensors so as to be distributed on the surface of the organism.

The sensors included in the monitor 10 use MEMS technology or the like and are compact and lightweight to the extent that when such sensors are attached to a human or other organism (body), the life and activity of the subject are barely obstructed. The sensors also need to have low power consumption so as to operate for an extended period using a lightweight battery. The power supply may be a small battery, a generator that uses external energy, such as a solar cell, a generator that generates power using body temperature, another biological reaction, or the activity of the organism, or may be a combination of the above.

The monitor 10 needs to have high precision and to be equipped with an automatic calibration function. The automatic calibration function has a function for automatically finding the measurement target part of the organism internal part from the surface of the organism and automatically tracking or rediscovering information from the target part without being affected by activity or the like of the organism (living organism).

Information (organism information) 150 for which measurement of a diabetic patient by the monitor 10 is desirable includes the glucose concentration in the blood, glycated hemoglobin concentration (HbA1c concentration) in the blood, glycated albumin concentration in the blood, blood pressure, blood oxygen content, cancer markers, and other factors related to health and life support.

Figure 2:
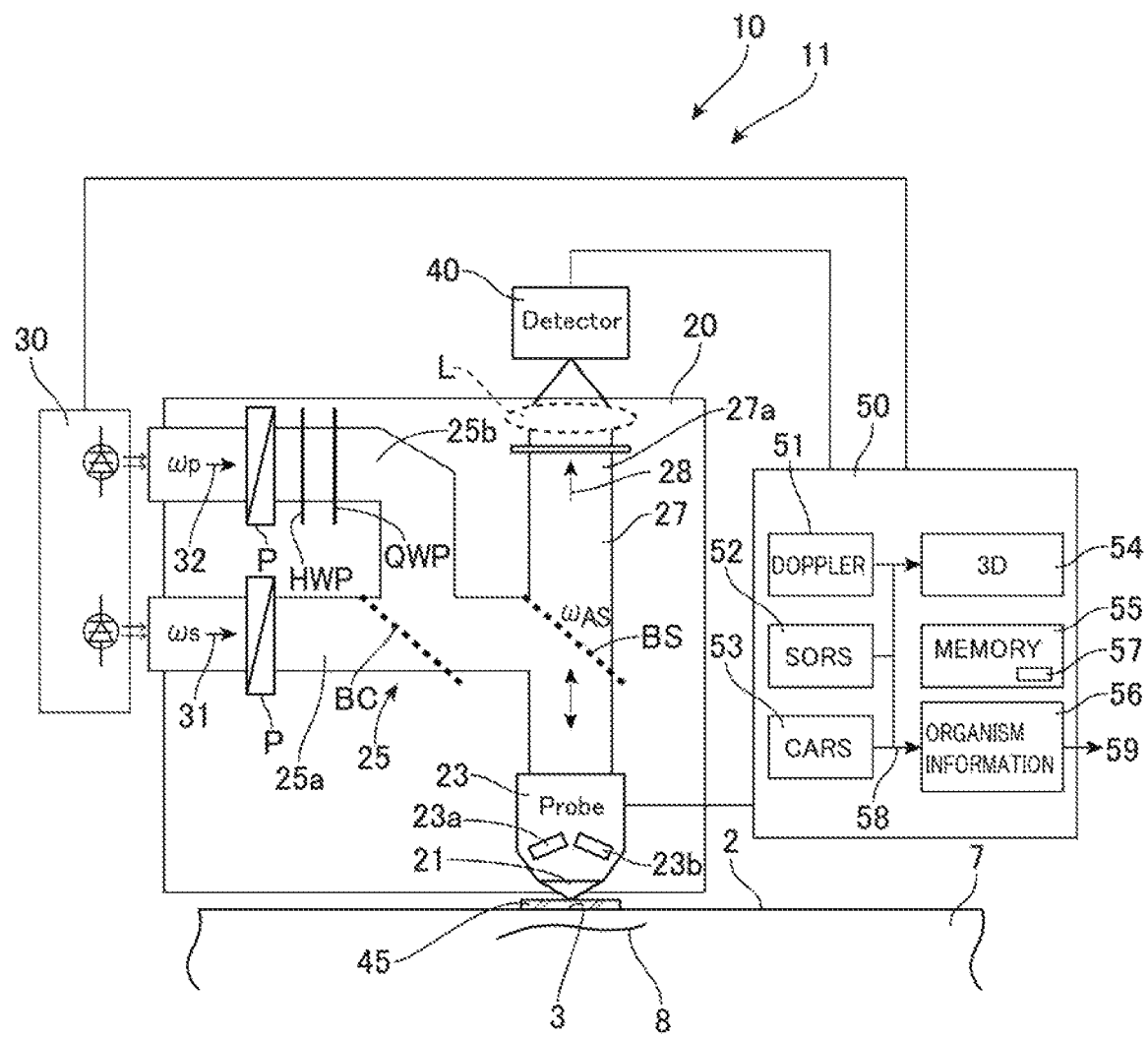
FIG. 2 is a block diagram showing a monitor.

FIG. 2 shows a Raman spectroscopic analysis unit 11 as an example of the monitor 10. This unit 11 includes an optical engine 20, a tunable laser engine 30, a detector 40, and a signal processing engine 50. Such components are packaged as chips, and the unit 11 is capable of being attached to the surface (skin) 2 of the organism (human body) 7 in a state where such chips are stacked.

The optical engine 20 is a MEMS optical chip and includes a probe including an observation window 21 attached to the skin 2, a unit 25 that emits (irradiates) a laser onto at least part of an observation region 3 of the skin 2 accessed via the observation window 21, and a unit 27 that detects scattered light produced by the emitted (irradiated) laser either intermittently so as to be distributed in two dimensions in the observation region 3 or from each of a plurality of observation spots continuously formed by scanning the observation region.

The laser emission unit (primary optical system) 25 is compatible with CARS and includes a first optical path 25a that guides Stokes light 31 of an angular frequency $\omega s$ obtained from the tunable laser engine 30 and a second optical path 25b that guides pump light 32 of an angular frequency $\omega p$ obtained from the tunable laser engine 30. The first optical path 25a and the second optical path 25b include a polarizer P, a half-wave plate HWP, a ¼ wavelength plate QWP, and the like. The laser emission unit 25 combines the Stokes light 31 and the pump light 32 using a dichroic beam combiner BC and emits laser light to the observation region 3 via the probe 23.

The laser engine 30 is a laser chip or an LED unit of a chip type that emits laser light of a plurality of wavelengths. As a variable wavelength laser engine, it is possible to use a Littrow laser engine, a Littman laser engine, or the like. As the laser engine 30, an engine capable of supplying variable wavelength Stokes light 31 and variable wavelength pump light 32 is especially desirable. One example of the wavelength range of the Stokes light 31 is 1000 to 1100 nm, with 900 to 1450 nm being more preferable. One example of the wavelength range of the pump light 32 is 700 to 800 nm. The laser engine 30 may generate laser light of such wavelength ranges using a combination of a plurality of light source units.

A detection unit (secondary optical system) 27 includes a beam separator BS that separates the anti-Stokes light with the angular frequency $\omega$ as supplied from the probe 23 and an optical path 27a that supplies scattered light (secondary light) 28, which is obtained from a plurality of observation spots formed so as to be distributed in two dimensions in the observation region 3, to the light detector 40. The detection unit 27 may include a lens L for collecting the scattered light 28 into the detector 40, a laser block filter, a diffraction grating, and the like. The detection unit 27 may include a flip mirror that divides and supplies the scattered light 28 to different types of detector, for example a CCD and a photodiode.

The light detector 40 may be a sensor where detection elements such as CCDs or CMOS are laid out in two dimensions. The light detector 40 may be a photodiode, with an InGaAs photodiode that has a fast response speed, low noise, and superior frequency characteristics being suitable. In particular, if the probe 23 is provided with a high resolution selecting function for the observation spots, a selecting function for the observation spots on the light detector 40 side may be unnecessary or may be a low resolution selecting function. Accordingly, it is possible to use a photodiode as the detector 40 and to output a signal with low noise.

The probe 23 includes an output unit 23a that forms a plurality of observation spots in the observation region 3 that can be accessed via the observation window 23 and an input unit 23b capable of selectively acquiring the scattered light 28 from the plurality of observation spots. The probe 23 uses an MD unit where MEMS type polygon mirrors are integrated as the output unit 23a, uses a combination of an MD unit and multi-fibers as the input unit 23b, and is designed so as to be capable of selectively acquiring the scattered light 28 from many observation spots in a state where there is no crosstalk.

Figure 3:
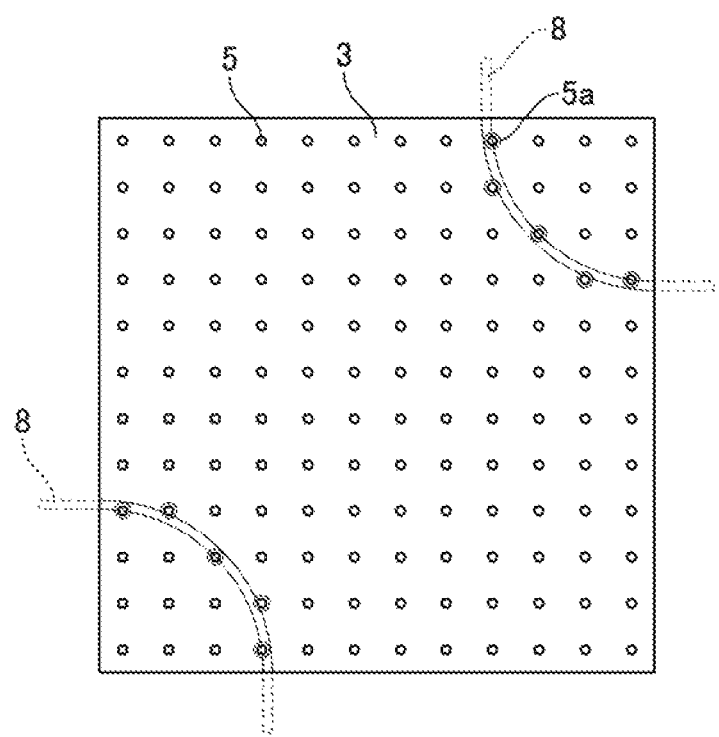
FIG. 3 is a diagram showing an observation region and observation spots.

FIG. 3 shows how a plurality of observation spots 5 are set in the observation region 3. In this example, 12 by 12 observation spots 5 are set with a pitch of 50 μm in a 600 μm by 600 μm observation region 3. The size of the observation region 3, and the pitch and number of the observation spots 5 are mere examples and are not limited to these values. The observation spots 5 do not need to have a regular pitch and may be continuously set using the MD unit. A high degree of reproducibility is required for the respective positions of the observation spots 5. It is also desirable for the pitch of the observation spots 5 to be sufficiently capable of detecting the size of the capillary vessels 8 (which for example have a diameter of several μm to several tens of μm) to be detected and to be capable of selectively acquiring information on the capillary vessels 8. Accordingly, the pitch of the observation spots 5 should preferably be around 1 to 1000 μm and more preferably around 10 to 100 μm.

The optical engine 20 may be provided with a function as 3D confocal Raman microscopy.

The signal processing engine 50 that controls the optical engine 20 includes a laser Doppler analyzing unit 51, a SORS analyzing unit 52, a CARS analyzing unit 53, a 3D profile unit (3D profiler) 54, a memory 55, and an organism information generating unit 56. The Doppler analyzing unit 51 and the SORS analyzing unit 52 function as the unit that limits, based on the scattered light 28 obtained from the plurality of observation spots 5, to the first observation spots 5a out of the plurality of observation spots 5 where it is determined or evaluated that scattered light 28 including information on capillary vessels 8 that are the target parts inside the organism 7 is obtained.

Based on the output of the laser Doppler analyzing unit 51 and the SORS analyzing unit 52, the 3D profiler 54 locks onto the first observation spots 5a that two-dimensionally cover the capillary vessels 8 and forms a profile in the depth direction for the first observation spots 5a. By doing so, a three-dimensional profile 57 of the capillary vessels 8 related to the observation region 3 is formed and stored in a memory 55. The three-dimensional profile 57 of the capillary vessels 8 is not limited to a single profile. The three-dimensional profile 57 may differ every time the probe 23 is placed, and may differ over time during probing, due to a change in posture or the like.

The CARS analyzing unit 53 functions as a unit that acquires spectra of at least one component from the first observation spots 5a and/or observation spots in the periphery of or about the first observation spots and outputs first information 58 showing the state (conditions) of the internal part of the organism 7 based on the intensity of the spectra. In addition, the CARS analyzing unit 53 functions as a unit that acquires spectra of a first component out of a plurality of parts with different depths from the organism surface 2 at the first observation spots 5a and/or the peripheries thereof and verifies the first observation spots 5a and further limits or updates the first observation spots 5a as necessary based on the intensities of the spectra of the first component.

The organism information generating unit 56 generates and outputs organism information 59 including the information 58 obtained from the CARS analyzing unit 53.

The CARS analyzing unit 53 in the present embodiment is equipped with a function as a SORS and, by emitting one out of the Stokes light 31 and the pump light 32 (for example, the Stokes light 31) at one of the first observation spots 5a and controlling the angle of one of the DM of the output unit 23a, emits the pump light 32 at a different angle to the Stokes light 31. The scattered light 28 of such laser lights is acquired at the input unit 23b that has superior positional selectivity (resolution) at observation spots 5 that are offset from the positions where the laser light is incident. By doing so, it is possible to obtain CARS spectra from a structure with different positions in the depth direction.

If the laser engine 30 is compatible with confocal Raman microscopy, it is possible to change the focal position of the laser in the depth direction. This means that it is possible to obtain a 3D Raman spectrum of an organism internal part, that is, subcutaneous tissues, from the organism surface (skin surface) 2.

If Raman spectra of blood flowing in a blood vessel are included in the different Raman spectra in the depth direction, it is possible to verify a 3D profile 57 obtained in advance. It is possible to determine whether a spectrum is a Raman spectrum of blood by selecting a Raman spectrum components (spectrum peaks) of components that have the highest concentrations in blood or the lowest concentrations in blood. For example, glucose is highest in blood vessels compared to subcutaneous tissues and dermis, so that it is possible to determine the position of a blood vessel by analyzing CARS spectra or 3D Raman spectra based on glucose concentration. In place of glucose, or in addition to glucose, it is possible to determine the positions of blood vessels by focusing on the Raman spectra of components that are mainly included in blood vessels such as the hematocrit which includes blood cells (white blood cells, red blood cells) or albumin.

If the position of a blood vessel (the blood vessel depth) can be determined, the Raman spectra at such position will reflect the components of blood, and it will be possible to continuously obtain information ("blood component information", "organism internal part information", or "first information") on the concentration of other components included in blood, for example, information on blood components such as glycated red blood cell concentration, in real time or at intervals of a minimal sampling time from the Raman spectra whose positions have been established. The distance (depth) and the positions (angles) between the monitor (sensor platform) 10 attached to the surface of the organism and the capillary vessels 8 will change depending on the posture and movement of the human body. For this reason, it is desirable to regularly repeat a process that finds the positions of blood vessels.

Figure 4:
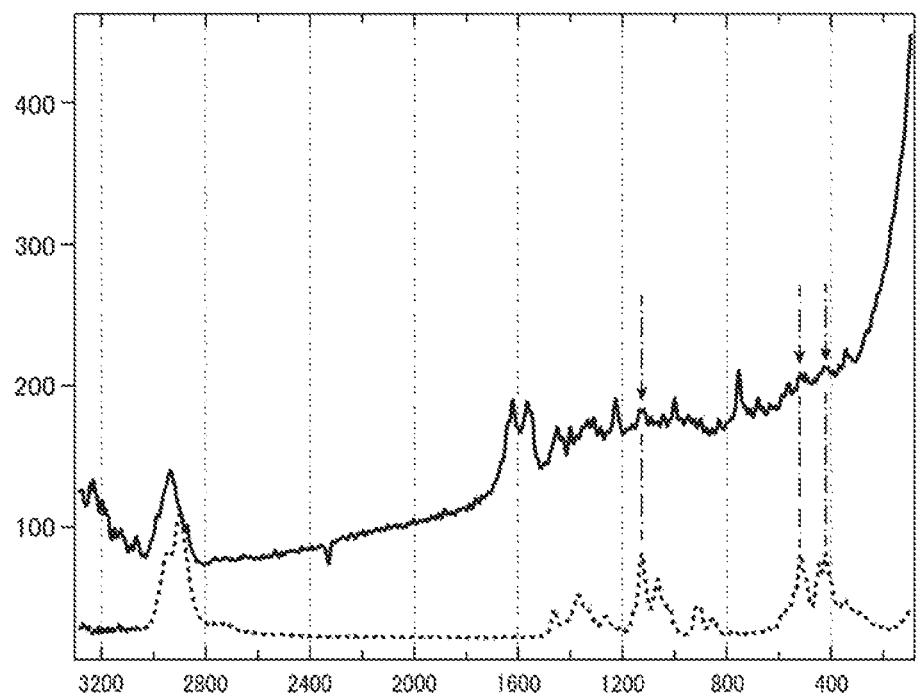
FIG. 4 is a diagram showing Raman spectra.

FIG. 4 shows a comparison between a Raman spectrum of glucose (broken line) and a Raman spectrum obtained from bovine blood (solid line). Raman shifts of glucose appear at around 400 cm$^{-1}$ and 1100 cm$^{-1}$, and are also observed in bovine blood. Accordingly, it can be understood that it is possible to measure the glucose concentration in blood from a Raman spectrum. Note that the spectra shown in FIG. 4 are spontaneous Raman scattering.

When attaching the probe 23 to the organism surface (skin) 2, it is desirable for the observation window 21 to tightly adhere to the skin 2 that is the surface of the organism with no gap and also for as little moisture as possible to be present between the observation window 21 and the skin 2. Although it is possible to measure using a means such as adjusting the laser power even when a gap or moisture is present, it is desirable to minimize such amounts to acquire information with high precision.

In the present embodiment, the probe 23 is placed in tight contact with the skin 2 via a diffusive porous membrane 45. Although the presence of moisture (sweat) due to dermal respiration acts as an obstacle to obtaining a Raman spectra including information on the organism internal part, by providing the diffusive porous membrane (transmissive membrane) 45 between the probe 23 and the skin 2, it is possible to continuously release moisture to the outside. The diffusive porous membrane 45 transmits the laser light 31 and 32 and the scattered light 28 and barely obstructs the observation described above. Since the diffusive porous membrane 45 is also elastic, the diffusive porous membrane 45 is capable of suppressing the production of a gap between the skin 2, even when the person moves. The diffusive porous membrane 45 may be stuck onto the probe or may be stuck onto the skin. Examples of the diffusive porous membrane 45 are PDMS (polydimethylsiloxane) and hybrid silica.

PDMS is one example of a polymer membrane material where the distance between polymer chains is large and therefore exhibits a high gas permeability coefficient. Accordingly, PDMS functions as a porous membrane with a fine aperture diameter and has been reported to be hydrophobic, have a high affinity to organic liquids, and to have superior selective permeability. Hybrid silica is a microporous organic-inorganic hybrid membrane with an average aperture diameter of 0.1 to 0.6 nm, uses silica that is hydrothermally stable up to at least 200° C. in several types of media as a base, and can be manufactured using short-chain crosslinked silane in a sol-gel process. It has been reported that hybrid silica is suited to the separation of gases and the separation of water and other small molecule compounds from various organic compounds, such as low molecular weight alcohols. The heat resistance is also high compared to PDMS, which makes hybrid silica suited to high temperature applications, for example, concentration where accumulation occurs at low temperature and releasing occurs at high temperature. The diffusive porous membrane 45 is not limited to such materials. It is also possible to interpose a semi-fluid, such as a gel, with the same functions in place of the diffusive porous membrane 45.

The monitor 10 that is the sensor platform may include, in addition to or in place of the Raman spectroscopic sensor 11, an ion mobility sensor (IMS) or a mass spectrometry sensor (MS) that analyzes components in dermal respiration. If the sensor platform 10 is a distributed-type sensor, an ion mobility sensor or mass spectrometry sensor for analyzing breath may be attached to the vicinity of the nostrils or inside the nostrils. Information from a plurality of sensors that are disposed in a distributed manner can be collected wirelessly or using wires.

Returning to FIG. 1, the analysis engine 120 analyzes the organism internal part information (information of interior of body) obtained by the monitor (sensor platform) 10 in combination with organism external information (information of exterior of body) obtained from the event tracking unit 140 and introduces physiologically active substances into the organism (human body) using the drug delivery unit 130.

It is desirable for the drug delivery unit (delivery unit) 130 to be automated, non-invasive and to be equipped with a plurality of drug introducing paths (channels), and to be capable of being easily attached to or stuck onto the organism (human body) 7. One example is a non-invasive insulin pump or injector that utilizes ultrasound using a MEMS, a field effect transistor, or nano-jets. Examples of prescription drugs 152 for diabetic patients are basal insulin and bolus insulin.

The drug delivery unit 130 may be attached to the surface of the body alongside the monitor 10. There is the risk that the physiologically active substance introduced into the body by the drug delivery unit 130 will affect the organism internal part information acquired by the monitor 10 before becoming absorbed or diffused in the body as expected. In such case, it is desirable for the drug delivery unit 130 to be attached to a position that is distant from the monitor 10, for example on the opposite side of the body. The information paths between the drug delivery unit 130, the analysis engine 120, and the monitor 10 may be wired or may be wireless and such elements may be connected directly, or indirectly via a computer network.

The event tracking unit 140 that provides the organism external information to the analysis engine 120 may be attached to the body, may observe actions of the body from outside, may be included in a server that manages the schedule of the patient, or may be a combination of such. A typical example of the event tracking unit 140 is a sensor or a sensor group that is capable of being attached to the body. The event tracking unit 140 includes functions that determine whether the patient has eaten and the content of meals using information obtained from image sensors or the like and/or recognize actions taken by the patient (as examples, has the patient started exercising, is working as normal, is sleeping, or is resting) using information obtained from acceleration sensors or the like.

The event tracking unit 140 may be equipped with sensors that acquire the body temperature of the patient, the humidity of the skin surface, and the temperature, humidity, wind speed, atmospheric pressure and the like outside the patient. It is also desirable for the event tracking unit 140 to be equipped with a function (learning function) that studies historical actions of the patient and is capable of predicting the actions of the patient (such as having a meal, exercise (training), daily business, sleeping, or resting) in the near future, such as a certain time later, one hour later, thirty minutes later, or several minutes later.

The analysis engine 120 is equipped with a function as a control unit of the system 1. The analysis engine 120 further includes a function (event predicting function) that predicts events that will dynamically occur for the patient himself/herself or in the periphery of the patient based on the organism external information obtained from the event tracking unit 140, a function (static event analyzing function) that considers the occurrence of normal (every day, routinely or static) events, and an event recognizing module 60.

The analysis engine 120 further includes a function (dosage estimating function) that considers the organism external information including the predicted events in addition to the organism internal part information obtained from the sensor platform 10 and decides and controls the type and amounts of physiologically active substances (for example, hormones such as insulin, prescription drugs, minerals, and nutrients) to be introduced from the drug delivery unit 130. The analysis engine 120 further includes a function (body parameter monitoring function) that acquires, for the function that decides the types and amounts of physiologically active substances, body parameters such as the content of any prescriptions, size characteristics of the body, and pre-existing conditions (disorders), from a database or the like and a function (calibration function) for calibrating.

The dosage estimating function that decides the types and amounts of physiologically active substances to be introduced or administered (dosed, injected) to the body includes a closed loop function that decides the types and amounts based on the organism internal part information and an open loop function that adds corrections to the output of the closed loop function based on a prediction function that includes the organism external information.

Figure 5:
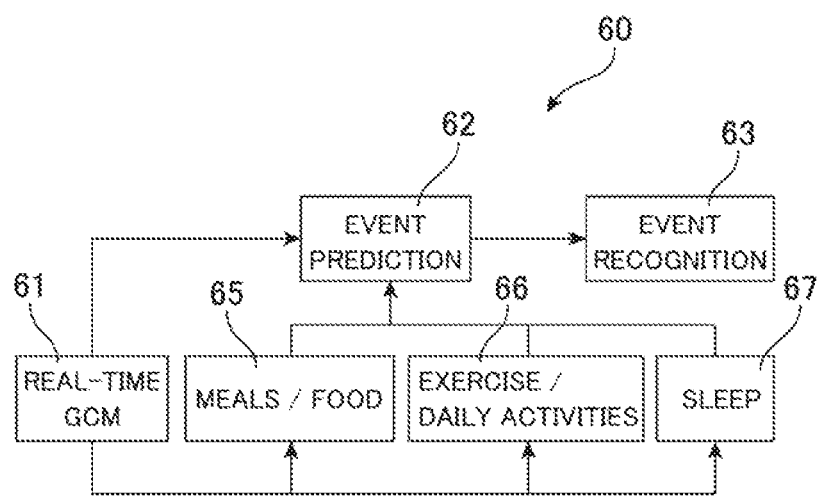
FIG. 5 is a block diagram showing an event recognizing module.

FIG. 5 shows an overview of the event recognizing module 60. This event recognizing module 60 may be provided in the analysis engine 120 or may be provided in the event tracking unit 140. The event recognizing module 60 processes information on real time GCM (Continuous Glucose Monitoring) obtained from the module 10 using event prediction information 62 and generates an event recognition 63 for controlling the medication (drug delivery) unit 130. The event prediction information 62 is generated based on information 65 showing that a meal or food has been taken, information 66 about everyday activities (daily life, daily business, daily work) being done, information 67 about sleep, and the like, which are obtained by the event tracking unit 140 or the like.

The analysis engine 120 further includes a function 68 that decides the types and amounts of physiologically active substances in accordance with an application or applications provided by a third party using an online store 154 or the like. Examples of applications provided by the online store 154 include a program for diabetic patients, a diet management program, a heart disease program, a stress monitoring program, a lifestyle management program, a prevention-diagnosis program, and an adapted diagnosis program. Here, myocardial infarction, cerebral infarction, liver dysfunction, renal dysfunction, and hyperlipidemia can be given as examples of diseases that can be determined or evaluated by the sensor platform 10 and treated or subjected to emergency response using physiologically active substances.

The analysis engine 120 also includes a function that exchanges information with a cloud service 156. The cloud service 156 includes a service that enables doctors or nurses and also family members or the like to monitor a patient online, and includes services such as online monitoring, a service that determines the type and amounts of medication by overriding events, a function that generates an event database, and a service that allows remote monitoring.

The analysis engine 120 can be realized using computer resources including a CPU and memory, may be an LSI or an ASIC, and also may be realized using a chip in which circuits can be reconfigured.

Figure 6:
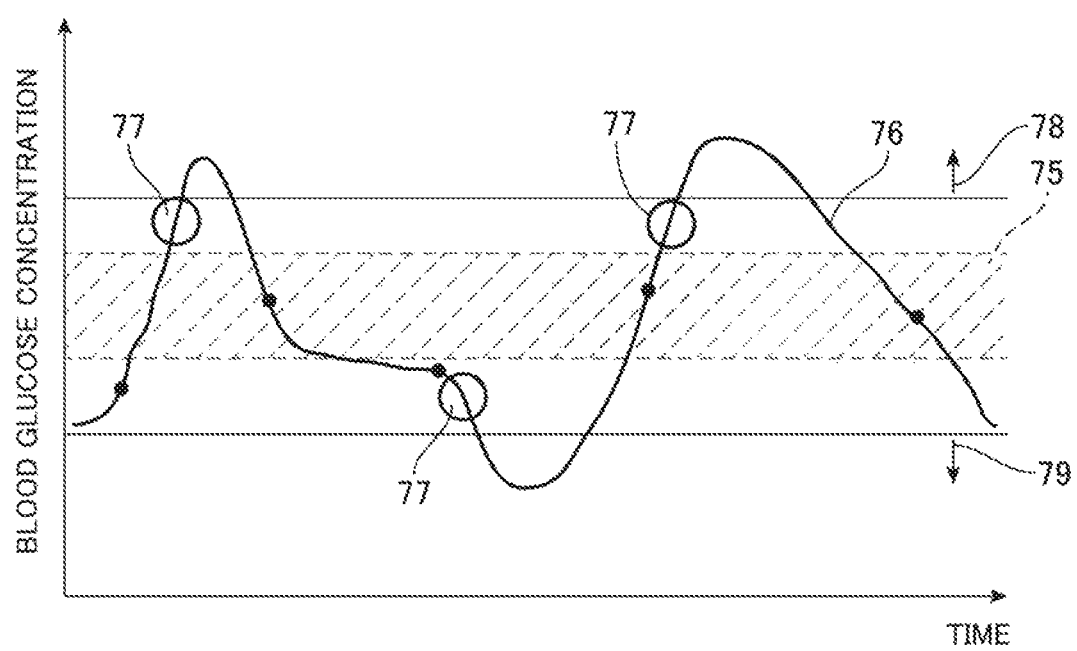
FIG. 6 is a diagram showing changes in glucose.

FIG. 6 shows an example of glucose changes in blood. The solid line shows a case where glucose in blood is investigated using some method and insulin is administered. When the glucose concentration in blood is measured using a puncture sensor (tap sensor), a delay (sensor lag) is produced in the measurements. Due to the administration (dosing) 77 of insulin being too late or too early, or the amount of insulin being too much or too little as a result, there is the risk of the glucose amount 76 reaching a hyperglycemic state 78 or a hypoglycemic state 79. In the worst case scenario, irreparable damage can be caused to the body, which may even lead to death. To avoid such situation, it is necessary to preemptively avoid the occurrence of states where the blood sugar level of a diabetic patient is changeable, and necessary for the patient to live with various limitations, such as avoiding acute exercise and taking regular meals and ingesting only a predetermined amount of calories.

On the other hand, in the health management system 1 according to the present embodiment, glucose in blood is continuously measured in real time by the monitor 10. Accordingly, it is possible to precisely control the administered amount of insulin with respect to the glucose concentration which is measured continuously. In addition, the event recognizing module 60 detects the occurrence of events (patient activities) such as exercise and meals and also predicts patient activities using a daily schedule and the outputs of various sensors. The analysis engine 120 decides the types and amounts of administered insulin so as to match the predicted state. This means that it is possible to control the glucose concentration in blood to a range 75 with a narrow width where there is little influence on health. This means that it become possible even for a diabetic patient to play sports and have meals in the same way as someone of good health conditions.

Figure 7:
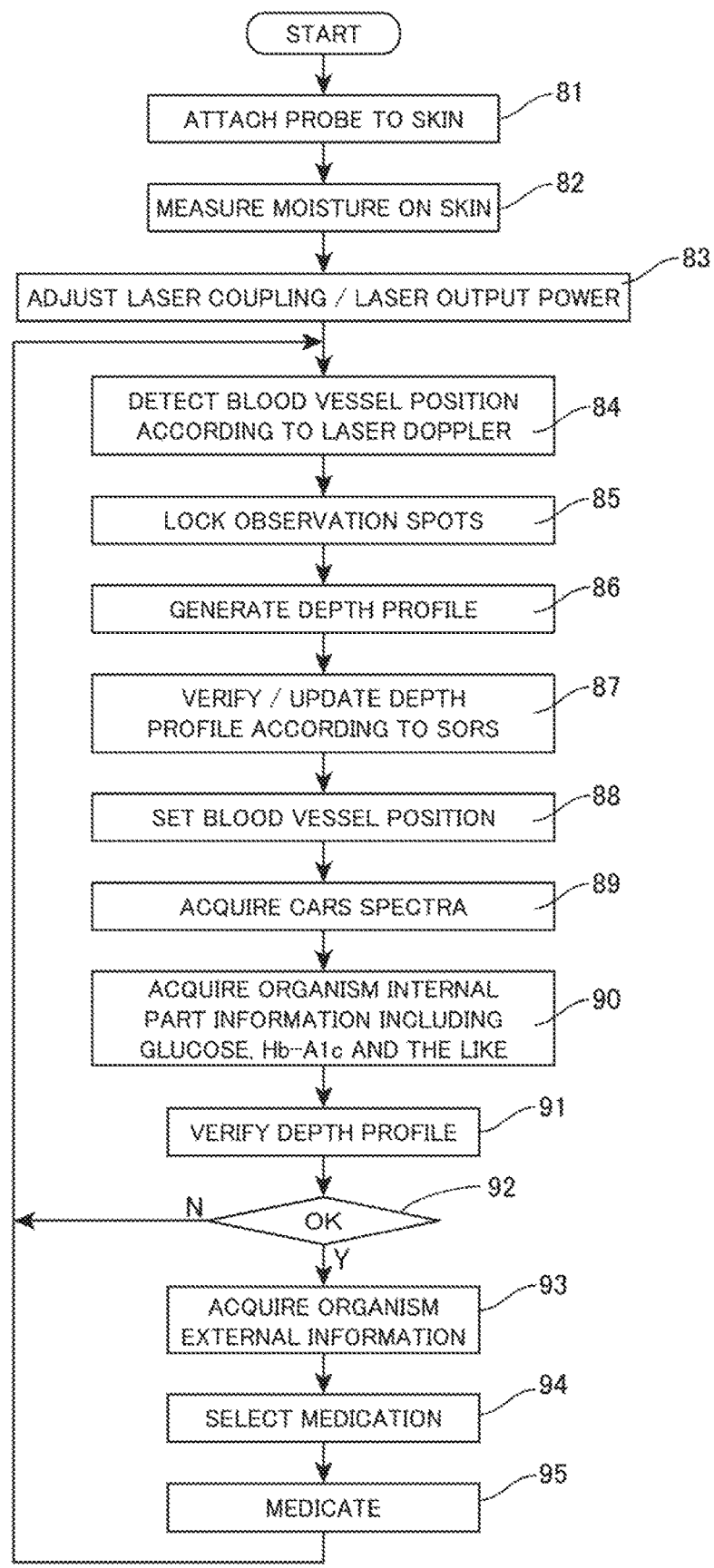
FIG. 7 is a flowchart showing the operation of the health management system.

FIG. 7 shows the major processes of the health management system 1 by way of a flowchart. In step 81, the observation window 21 of the probe 23 of the monitor 1 is attached to the surface of the skin 2 via the PDMS 45. In step 82, the Raman spectrum of moisture on the skin 2 in the observation region 3 visible in the observation window 21 is measured. As one example, it is possible to measure the amount of moisture at the surface and inside the skin using a confocal method, and it is also possible to measure the distance to the skin. In step 83, the output (power) of the laser used in subsequent measurements is adjusted according to the amount of moisture at the skin surface and distance to the skin surface. Since the penetration of the laser will change if there is a lot of moisture on the surface of the skin 2 or a gap is present between the skin 2 and the observation window 21, it is desirable to adjust the output power of the laser. It is also possible to find the amount of moisture on the surface of the skin 2 by measuring the electrical conductivity (conductivity).

In step 84, the laser Doppler analyzing unit 51 is used to determine the observation spots 5a where blood flow is detected out of the observation spots 5 in the observation region 3 using a laser Doppler method. By limiting to or setting the observation spots 5a where blood flow is detected, it is possible to specify the positions of capillary vessels 8 in the observation region 3 and to identify observation spots 5a positioned directly above or in the vicinity of the capillary vessels 8. As one example, it is possible to emit pump laser light 32 with a wavelength of around 800 nm onto the entire observation region 3, to acquire spectra (Rayleigh scattering) of the scattered light 28 obtained from the respective observation spots 5, and to determine the presence of blood flow if a spread of Doppler shift frequencies of light that has been scattered by red blood cells is observed in such spectra. The laser light 32 may be separately emitted onto the respective observation spots 5 using the DM module 23a.

In step 85, the observation spots (first observation spots) 5a to be measured in the following steps are limited (narrow downed) and locked onto as the measurement targets via the first observation spots 5a. In step 86, the 3D profiler 54 generates, from the Doppler shift data obtained from the locked-onto observation spots 5a and in accordance with a mathematical model, a depth profile showing the capillary vessels 8 below the observation spots 5a that have been locked onto.

Next, in step 87, the profiler 54 also verifies the profile in the depth direction of the observation spots 5a using the SORS analyzing unit 52. With spatially offset Raman spectroscopy (SORS), by emitting laser light onto the observation spots 5a and acquiring the scattered light 28 away from the observation spots 5a at observation spots 5 in the periphery of the observation spots 5a, Raman spectra are obtained from the deep tissues below the skin 2. It is also possible to adjust the incident angle of the laser and acquire Raman spectra for generating a profile in the depth direction.

In step 88, once the 3D profile 57 that includes depth profiles using the locked observation spots 5a is obtained, the profiler 54 decides the positions in the depth direction to be measured (the target parts) where capillary vessels 8 are likely to be present. By doing so, the three-dimensional positions of the target parts are decided.

In step 89, the CARS analyzing unit 53 acquires CARS spectra from the measured positions using coherent anti-stokes Raman spectroscopy (CARS). The CARS analyzing unit 53 emits (incidents, irradiates) a variable wavelength laser as the Stokes light 31 and/or the pump light 32 selectively onto the locked observation spots 5a or the observation spots 5 in the periphery of the locked observation spots 5a so as to intersect at the set depths. By doing so, from the locked observation spots 5a, it is possible to acquire the anti-Stokes Raman scattered light 28 from components that are present at the set depth and that match the wavelength conditions set by the Stokes light 31 and the pump light 32. This means that the detector 40 is capable of detecting a CARS spectrum from the tissue at positions below the skin where the capillary vessels 8 are likely to be present. Accordingly, information on the capillary vessels 8 is obtained as low noise information without being diluted by or averaged with Raman spectra from other tissues.

To supply the scattered light 28 from the individual observation spots 5a to the detector 40, it is desirable to use the input unit 23b equipped with a combination of multi-fibers capable of forming multifocal points and a DM or a MEMS type shutter to shut out the scattered light 28 from other observation spots 5.

In addition, by giving the Stokes light 31 and the pump light 32 variable wavelengths and limiting or narrowing the emission (incident) position and area to the locked observation spots 5a or the peripheries of the observation spots 5a respectively, positional resolution and wavelength selectivity are unnecessary at the detector 40. This means that it is possible to use a photodetector that has a fast response speed and high precision. This means that it is possible to supply the Stokes light 31 and the pump light 32 as light in short pulses, and as one example, it is possible to supply pulsed light in picosecond or femtosecond units.

Accordingly, it is possible to preemptively prevent damage to the skin 2 by laser light and possible to acquire information from the capillary vessels 8 continuously for a long time while suppressing the influence on the body. It is also possible to further reduce the influence of the laser light on the skin 2 by placing a porous membrane such as the PDMS 45 between the system 1 and the skin 2.

In step 90, the CARS analyzing unit 53 extracts information on glucose, hemoglobin HbA1c, and the like from CARS spectra and supplies such information as the first information 58 to the organism information generating unit 56. The organism information generating unit 59 aggregates the first information 56 on blood and if necessary, information collected by the profiler 54 in the process of generating a 3D profile, and supplies the aggregated information to the analysis engine 120 as the organism internal part information 59.

In step 91, the CARS analyzing unit 53 acquires CARS spectra for which the depth set as the measurement target (target part) is changed at fixed intervals. From the glucose concentration included in the Raman spectra that change in the depth direction (the vertical direction), it is determined whether a depth spectrum of the target part is suitable as the spectrum of a blood vessel compared to spectra of parts at other depths. By doing so, it is possible to always verify the depth profile 57. In step 92, when information obtained from a target part is not suitable as a blood vessel, the processing returns to step 84 and the 3D profile 57 is updated and regenerated.

The Raman spectrum component used to verify the depth profile 57 is not limited to glucose and may be hematocrit, albumin or other component such as that is present in an even higher concentration in a blood vessel than the periphery tissues.

When acquiring CARS spectra by changing the depth direction, the CARS analyzing unit 53 may change the angle of the Stokes light 31 or the pump light 32 and acquire CARS spectra at a position that is shifted (offset) from a predetermined observation spot 5*a*. By acquiring CARS spectra that have been spatially offset (SOCARS spectra), it is possible to further improve the precision of the profile in the depth direction.

It is also possible to acquire spectra using resonance Raman spectroscopy in place of CARS or in addition to CARS. By combining data of a plurality of Raman spectrometry sensors 11, 3D Raman spectra may be acquired.

In step 90, the analysis engine 120 is capable of acquiring organism internal part information including all components that can be estimated from Raman spectra which are not limited to glucose and may be chemical components aside from glucose, cells such as red blood cells, and blood components such as proteins like albumin and others that are present in blood flowing in blood vessels.

In step 93, the analysis engine 120 also acquires organism external information from the event tracking unit 140 and in step 94 determines the types and amounts of physiologically active substances to be given as medication by the medication unit 130 based on the organism internal part information and the organism external information. In step 95, the medication unit 130 administers (doses) predetermined physiologically active substances, for example insulin, based on the analysis result of the analysis engine 120.

As described above, the health management system 1 is a non-invasive health and vitality control platform having a continuous closed loop, includes a non-invasive spectrometer whose wavelength is programmable, further has a body activity and event tracking unit, a control unit, and a medication unit (drug delivery unit) in an integrated form, and is capable of automatically carrying out automatic adjustment of the measuring part. A non-invasive optical mass spectrometric technique is used for measurement based on blood. The monitor 10 that is the sensor platform is a MEMS-based optical apparatus that has a tunable laser and uses highly permeable membrane tissue (thin film) at a part that contacts the human body.

This system 1 is used as a platform and has expandability in that new methods (methods of treatment) and management methods can be downloaded and used.

The invention claimed is:

1. A monitor that monitors a state of an organism internal part from a surface of the organism, comprising:
   a probe including an observation window configured to be attached to the surface of the organism;
   a light source that is configured to emit lasers that have a wavelength of a stokes light and a wavelength of a pump light onto at least part of an observation region on the surface of the organism accessed via the observation window;
   a detector that is configured to detect CARS light caused by emission of the lasers of the stokes light and the pump light at a depth in the organism to obtain a depth profile of the organism; and
   a profiler that is configured to acquire spectra of at least one component of the depth profile that has a highest concentration or a lowest concentration in a target part to find the target part according to a change in the concentration of the at least one component in a depth direction; and
   a CARS analyzer that is configured to acquire spectra of the CARS light at a depth set as the target part and output first information showing the state of the target part of the organism internal part based on a highest peak or a lowest peak of intensities of the spectra of the CARS light.

2. The monitor according to claim 1, wherein the at least one component includes at least one of glucose, hematocrit and albumin.

3. The monitor according to claim 1, wherein the target part is a capillary.

4. The monitor according to claim 1, further comprising a diffusive porous membrane that is configured to attach the observation window of the probe to the surface of the organism.

5. A system comprising:
   the monitor according to claim 1; and
   a delivery device that is configured to provide a physiologically active substance to the organism based on the first information.

6. The system according to claim 5 further comprising:
   a processor that is configured to perform a process including:
   monitoring a behavior to acquire or predict an external state of the organism; and
   controlling an amount or type of physiologically active substance provided to the organism from the delivery device according to information from of the monitoring the behavior in addition to the first information.

7. The system according to claim 6, wherein the process further includes outputting the first information and an operating state of the delivery device to outside.

8. A control method for a system including a monitor that monitors a state of an organism internal part from a surface of the organism,
   the monitor including:
   a probe including an observation window that is configured to be attached to the surface of the organism;
   a light source that is configured to emit lasers that have a wavelength of a stokes light and a wavelength of a pump light onto at least part of an observation region on the surface of the organism accessed via the observation window; and
   a detector that is configured to detect CARS light caused by emission of the lasers;
   wherein the method comprises:
   emitting the lasers of the stokes light and the pump light at a depth in the organism to obtain a depth profile of the organism; and
   acquiring spectra of at least one component of the depth profile that has a highest concentration or a lowest concentration in a target part to find the target part according to a changing the concentration of the at least one component in a depth direction; and
   acquiring spectra of the CARS light at a depth set as the target part and outputting first information showing the state of the target part of the organism internal part based on a highest peak or a lowest peak of intensities of the spectra of the CARS light.

9. The method according to claim 8,
wherein the acquiring includes finding a capillary based on at least one of depth profiles of glucose, hematocrit and albumin.

10. The method according to claim 8,
wherein the system further includes a delivery device that is configured to provide a physiologically active substance to the organism based on the first information,
and the method further comprises selecting a physiologically active substance and an amount to be delivered by the delivery device based on the first information.

11. The method according to claim 10, further comprising:
monitoring a behavior to acquire or predict an external state of the organism; and
selecting the amount or type of physiologically active substance delivered by the delivery device based on information on the external state in addition to the first information.

\* \* \* \* \*